United States Patent
Stenzel et al.

(10) Patent No.: US 9,901,726 B2
(45) Date of Patent: Feb. 27, 2018

(54) CONNECTOR AND MEDICAL DEVICE FOR EXTRACORPOREAL BLOOD TREATMENT COMPRISING SUCH CONNECTOR

(71) Applicant: B. Braun Avitum AG, Melsungen (DE)

(72) Inventors: Bruno Stenzel, Hatten (DE); Andreas Schade, Rotenburg (DE)

(73) Assignee: B. BRAUN AVITUM AG, Melsungen (DE)

( * ) Notice: Subject to any disclaimer, the term of this patent is extended or adjusted under 35 U.S.C. 154(b) by 199 days.

(21) Appl. No.: 13/910,357

(22) Filed: Jun. 5, 2013

(65) Prior Publication Data

US 2013/0328304 A1    Dec. 12, 2013

(30) Foreign Application Priority Data

Jun. 6, 2012 (DE) .......................... 10 2012 104 931

(51) Int. Cl.
  *A61M 39/10*  (2006.01)
  *A61M 1/14*  (2006.01)
  (Continued)

(52) U.S. Cl.
  CPC .............. *A61M 39/10* (2013.01); *A61M 1/14* (2013.01); *A61M 39/1011* (2013.01);
  (Continued)

(58) Field of Classification Search
  CPC .. A61M 2039/1027; A61M 2039/1033; A61M 2039/1077; A61M 39/10; A61M 39/1011; A61M 39/12
  See application file for complete search history.

(56) References Cited

U.S. PATENT DOCUMENTS 1,849,604 A    3/1932    Weatherhead, Jr.
4,610,468 A    9/1986    Wood
(Continued)

FOREIGN PATENT DOCUMENTS

CN    1694654    11/2005
DE    196 05 260 A1    11/1996
(Continued)

OTHER PUBLICATIONS

European Search Report dated Aug. 27, 2013 for Application No. EP 13 16 7897.
(Continued)

*Primary Examiner* — Tatyana Zalukaeva
*Assistant Examiner* — Kai Weng
(74) *Attorney, Agent, or Firm* — RatnerPrestia

(57) ABSTRACT

A connector adapted to be detachably arranged in an opening of a housing of a medical device and including a connecting element to which a single-use article can be connected outside of the housing is disclosed. Via a hollow link portion the connecting element is connected to a coupling adapted to be inserted into the interior of the housing through the opening of the housing. Moreover, the connector includes a spring element adapted to be detachably arranged at the link portion so that the connector is supported at the housing to be axially resilient via the spring element. A medical device for extracorporeal blood treatment including such connector as an interface to a single-use article, for example, is also disclosed.

5 Claims, 4 Drawing Sheets

(51) Int. Cl.
 *A61M 39/12* (2006.01)
 *F16B 21/18* (2006.01)
(52) U.S. Cl.
 CPC ..... *A61M 39/12* (2013.01); *A61M 2039/1027* (2013.01); *A61M 2039/1033* (2013.01); *A61M 2039/1077* (2013.01); *F16B 21/186* (2013.01)

(56) References Cited

U.S. PATENT DOCUMENTS

| | | |
|---|---|---|
| 4,640,534 A | 2/1987 | Hoskins et al. |
| 4,844,409 A | 7/1989 | Lackler et al. |
| 6,030,003 A | 2/2000 | Peed et al. |
| 7,080,672 B2 | 7/2006 | Fournie et al. |
| 2002/0185327 A1 | 12/2002 | Morykon |
| 2004/0171979 A1 | 9/2004 | O'Neil |

FOREIGN PATENT DOCUMENTS

| | | |
|---|---|---|
| DE | 196 14 684 A1 | 12/1996 |
| WO | WO 92/08060 A1 | 5/1992 |
| WO | WO 96/25214 | 8/1996 |

OTHER PUBLICATIONS

German Search Report dated Jan. 17, 2013 for Application No. 10 2012 104 931.9.
European Exam Report for EP 13 167 897.1 dated Jul. 17, 2014.
European Exam Report for EP 13 167 897.1 dated Aug. 14, 2015.
European Office Action, with translation, for EP 13 167 897.1 dated Jul. 12, 2016.
Chinese Exam Report, with translation, for CN201310222265.1 dated May 6, 2016.

CONNECTOR AND MEDICAL DEVICE FOR EXTRACORPOREAL BLOOD TREATMENT COMPRISING SUCH CONNECTOR

CROSS REFERENCE TO RELATED APPLICATIONS

This application claims priority to German Patent Application No. DE 10 2012 104 931.9 filed Jun. 6, 2012, the contents of such application being incorporated by reference herein.

FIELD OF THE INVENTION

The invention relates to a connector for being detachably mounted in an orifice of the medical device comprising a connecting element to which a single-use article can be connected outside the housing.

The invention further relates to a medical device for extracorporeal blood treatment comprising such connector.

BACKGROUND INFORMATION

In medico-technical devices it is frequently necessary to provide interfaces to single-use articles. Said interfaces can become necessary, for example, to allow for pressure and/or temperature measuring and monitoring in the single-use article or the passage for fluids or gases. Interfaces can also enable optically, acoustically and/or mechanically acting measuring systems to be incorporated in circulations, or filters and further volumes can be incorporated in a tube system. For obtaining a standardized configuration of said interfaces in plural cases a connection is made by means of the standardized Luer cone.

In medical devices for extracorporeal blood treatment (dialysis) for example single-use articles are used forming at least of the intake and discharge lines and plural air separators a so called transition system by which the patient's blood is fed back to a dialyser and to the patient. Those transition systems are exchanged after each treatment and are not re-used for other patients.

In the field of extracorporeal blood treatment it further belongs to the state of the art to provide the single-use article with a female Luer connector adapted to be connected to the male counter-piece provided at the medical device for monitoring the pressure of the extracorporeal circulation. This connection has to be newly made for each treatment which means that the part of the connection provided at the medical device can be worn or damaged by improper use. In such case it must be possible to exchange the connecting part provided at the medical device.

The part provided at the medical device can be made of different materials. It is known, for example, to use stainless steels, steels having a surface coating for corrosion protection (e.g. chromium or nickel plated), base metals having a surface coating (e.g. anodizing) or plastic materials. Moreover, the connectors can be fastened in the housing of the medical device in various ways, which can be performed especially by gluing or screwing. The selected fastening has to absorb forces acting in the circumferential direction as they occur when screwing on the single-use article. Furthermore, the fastening has to be capable of absorbing axially acting forces e.g. by tensile forces on the single-use article. On the whole, the fastening should also be detachable, however, so as to be able to exchange the connector if needed.

An inexpensive solution for manufacturing a connector constitutes the fabrication as an out-of-tool part in injection molding technique. Possible material variants are thermoplastics such as POM, PA, PP, PEEK, PPSU, PSU or PPS. However, the properties of a connector manufactured in this way impede applying the fastening techniques currently known as state of the art or conflict with the requirement of exchangeability.

SUMMARY OF THE INVENTION

Therefore it is an object of the invention to provide a connector that meets the afore-mentioned basic requirements while being easy to manufacture and to assemble. It is another object of the invention to provide a medical device comprising such connector as interface.

The connector according to aspects of the invention serves for coupling a single-use article to the housing of a medical device and comprises a connecting element to which the single-use article can be connected outside the housing. In accordance with the invention, the connecting element is connected to the coupling via a hollow link portion or a hollow land. The coupling can be introduced to the inside of the housing through the opening of the housing. The connector further comprises a spring element adapted to be detachably mounted to this link portion so that the connector is supported to be axially resilient on the housing.

A support of the spring element on the housing may include a fitting at the inside of a housing wall and/or a fitting of the spring element within the housing wall or appropriately shaped thickenings of the housing wall. Also additional components being arranged at a housing wall to hold, to fix and/or to tension the spring element relative to the connector have to be regarded as a part of the housing. The spring element according to aspects of the invention thus satisfies, on the one hand, the function of a circlip and, on the other hand, the function of a flexible spring.

The connector can be axially fixed at the housing by the attachable spring element, wherein manufacturing tolerances and variations of the clamping length can be compensated by a spring element in the form of a disk spring. Furthermore the connector can be axially loaded by tensile forces without the connector being damaged when the single-use article attached thereto is pulled, for example.

The connector further can have, especially at the link portion, means for rotary fixing of the connector within the opening of the housing.

The means for rotary fixing or radial locking of the connector within the opening of the housing constitute torsional protection in the circumferential direction and further can be used to specifically align the connector at the housing. This can be of advantage, for example, when other systems are attached at the coupling.

In an advantageous configuration the spring element can be used not only for axially fixing the connector within the housing opening but also simultaneously as means for rotary protection in the case of appropriate configuration.

The spring element can be adapted to be axially or radially slipped onto the link portion and at least one groove can be provided at the link portion for axial form-fit fixing of the spring element.

The spring element can be in the form of a disk or a leaf spring, can have a central opening and can be provided with a segment-shaped recess or a radial slit reaching to the central opening so that the spring element can be spread apart for being put into the groove in the link portion. This operation takes place when assembling the connector at the housing, but the spring element can also be simply removed from the groove again, whereupon the connector can be detached from the housing again. Hereby quick assembly and disassembly without the need of tools is possible, wherein no drying times have to be taken into account for example by the otherwise common gluing of component parts. Moreover the component parts of the connector are relatively immune to improper use.

The link portion can have a round or rectangular external cross-section, wherein a rectangular external cross-section can be used already for rotary fixing of the link portion within the opening of the housing, when the opening equally has a corresponding shape. The means for rotary fixing the connector within the opening in the housing can also comprise specifically shaped locking geometries within the opening and at the link portion, however. For instance, at the link portion a lug is provided and within the opening in the housing a groove is provided into which the lug is axially inserted.

In an embodiment of the invention the coupling, the connecting element and the link portion are shaped as one-piece molded plastic part which renders the manufacture of the connector inexpensive. In this way, the spring element, too, can be manufactured inexpensively of plastic material. Possible material variants are proven thermoplastics such as POM, PA, PP, PEEK, PPSU, PSU or PPS. The design of the connector permits being appropriate to plastic material.

Moreover, the connector can be encoded in color by adding color particles which can also be realised in an inexpensive manner.

The invention further comprises a medical device for extracorporeal blood treatment comprising a housing, the housing having at least one opening into which a connector according to aspects of the invention is introduced. Such medical device thus provides a standardized interface for connecting a single-use article such as a bypass system. Any systems can be connected to the coupling within the housing, which can especially be a manometer.

When the medical device is designed so that the spring element is accessible from outside of the housing, the connector can be exchanged even without opening the device.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1A:
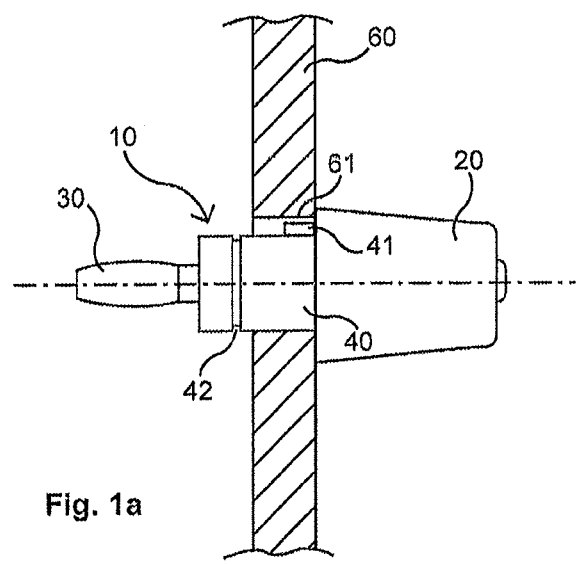
FIG. 1a a schematic side view of a first embodiment of a connector prior to mounting a spring element.
Figure 1B:
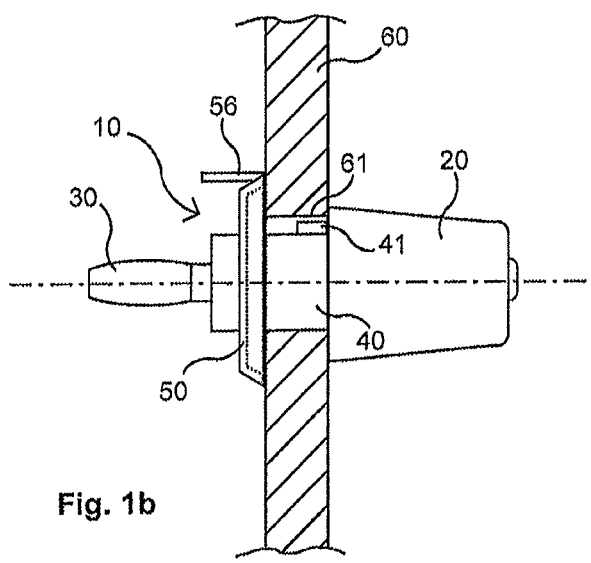
FIG. 1b a connector according to FIG. 1b including a spring element mounted from inside.
Figure 2:
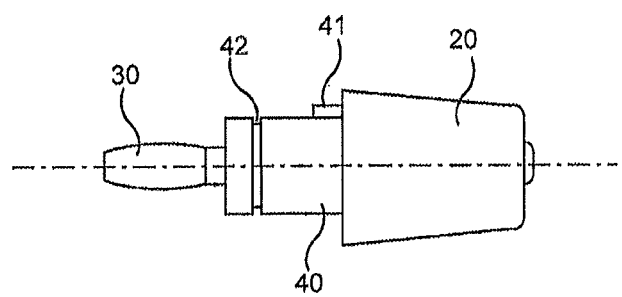
FIG. 2 a schematic side view of a connector.

FIG. 1a shows a first embodiment of a connector 10 according to aspects of the invention which is introduced already within an opening in a housing or a housing wall 60 of a medical device but has not yet been fixed by a spring element. FIG. 1b shows the same connector 10 with a mounted spring element 50. FIG. 2, on the other hand, shows the connector 10 being detached from the housing 60.

The connector 10 includes a connecting element 20 and a coupling 30 interconnected by a hollow link portion 40. Preferably the connecting element 20 is a male Luer cone onto which a single-use article in the form of a tube can be slipped. The coupling 30 can also be in the form of such tube connection. The connector 10 serves for coupling a single-use article (not shown) outside the housing 60 of the medical device to a means (not shown), e.g. measuring means, within the housing 60.

The coupling 30 is positioned inside the housing 60 while the connecting element 20 is arranged outside the housing 60. The connecting link portion 40 penetrates the housing 60 in an opening, wherein a portion of the link portion 40 protrudes into the interior of the housing 60. At this portion at least one groove 42 is provided, as it is also visible in FIG. 2. The groove 42 can be designed to be completely or intermittently circumferential, e.g. at least two opposed grooves are provided at the link portion. Into this groove 42 a spring element 50 is inserted in the representation of FIG. 1b. The spring element 50 is disk-shaped so that is can be clamped between the groove 42 and the inside of the housing 60. This disk shape is shown in broken lines in FIG. 1b and the connecting element 20 is adjacent from outside to the housing 60 and is biased against the outer wall of the housing 60 by the spring force of the spring element 50. The connector 10 is radially supported in the housing opening via the link portion 40.

Figure 1C:
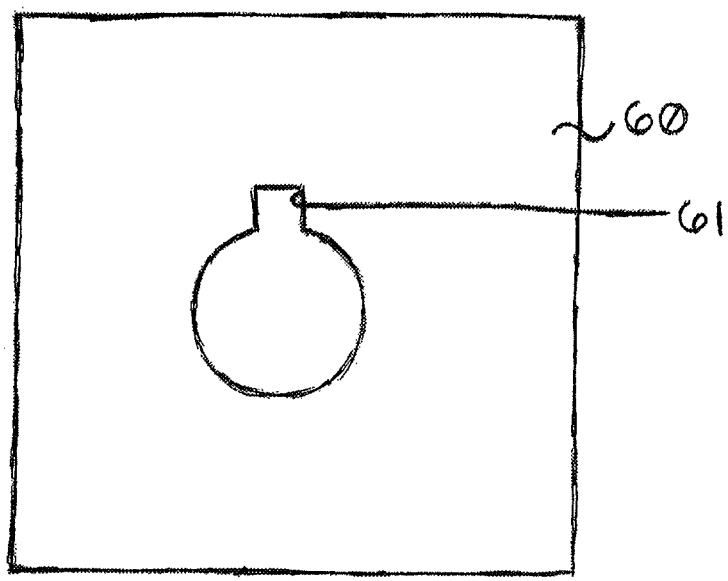
FIG. 1c depicts a housing wall of a medical device viewed from the inside having an opening with an axially extending groove.

Furthermore, at least one lug 41 or a tongue engaging in a corresponding axially extending groove 61 within the opening in the housing 60 is provided at the link portion 40, thereby the link portion 40 and thus the connector 10 being fixed inside the housing 60 in the circumferential direction. FIG. 1c depicts the housing 60 from the inside and an embodiment of the axially extending groove 61 as part of the opening.

Figure 3:
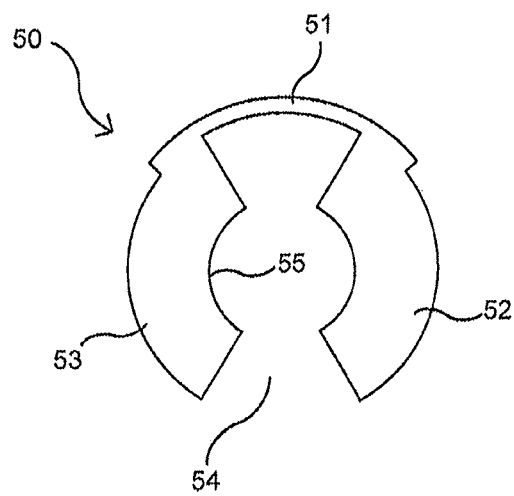
FIG. 3 a schematic top view of a spring element.

An embodiment of the spring element 50 is shown in a top view in FIG. 3. The spring element 50 is formed on the whole like a disk spring. The outer edge of the spring element 50 is inclined, as shown in FIG. 1b, and causes the spring-elastic deformation of the spring element 50. In addition, the spring element 50 centrally includes an opening 55. Next to this opening 55 two lateral parts 52 and 53 are arranged and interconnected via a connecting arc 51. Opposite to the connecting arc 51 a segment-shaped recess 54 protruding to the opening 55 is provided. The connecting art 51 is elastic so that the two lateral parts 52 and 53 can be spread apart against a spring force of the connecting arc 51.

For assembling the connector 10 to the housing 60 the coupling 30 and the link portion 40 are pushed through the opening into the housing 60 so that the outer connecting element 20 contacts the housing 60 and the groove 42 is located at the link portion 40 inside the housing 60. Subsequently the spring element 50 is introduced laterally e.g. from above into the groove 42 in the link portion 40 by pressing the recess 54 onto the link portion 40. The flanks of the recess 54 open radially outwardly so that the spring element 50 is spread apart when being slipped onto the link portion 40. The two lateral parts 52, and 53 are pressed apart and the spring element 50 is located with the inner edges of the opening 55 in the groove 42. As already mentioned, the spring element 50 is introduced so that a spring force in the axial direction is generated by the disk shape.

In order to dismount the connector 10 the spring element 50 can be removed from the groove 42 again. For this, small gripping areas or bulges can be provided to be able to conveniently grip the spring element 50. In the embodiment of FIG. 1b a grip element 56 is provided in the upper area, for example. Instead of the grip element also an eyelet can be provided into which a drawing means can engage.

In the embodiment of FIGS. 1a and 1b the spring element 50 thus can be assembled from inside, i.e. an access to the interior of the housing 60 must be possible to mount or dismount the connector 10 in an opening of the housing wall. For this purpose the respective housing wall can be removed, for instance, so as to get to its rear side.

Figure 4:
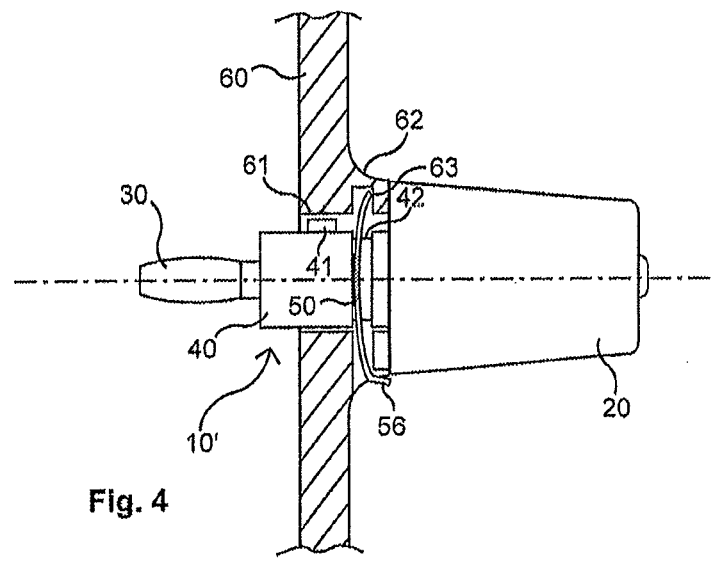
FIG. 4 a schematic side view of a second embodiment of a fixed connector including a spring element mounted from outside.

In a second embodiment of the invention the spring element 50 can be mounted from outside, on the other hand. This can be realized in different ways, FIG. 4 showing a possible embodiment of such connector 10'. To be able to mount and dismount the spring element 50 from outside at least in the area of the outer connecting element 20 at the outside of the housing 60 a bulge or elevation 62 is formed, which can also be referred to as support element, to which the connecting element 20 is adjacent and on which it is supported. Preferably it is a circular elevation the circumference of which approximately corresponds to the circumference of the Luer cone 20. Thus the elevation 62 can be transformed into the Luer cone 20 to be flush without any step/edge.

The opening into which the connector 10' is to be introduced extends through the housing wall 60 and the support element 62. Furthermore, within this opening again a groove 61 is provided which together with a lug 41 provided at the link portion 40 ensures a protection against rotation of the connector 10 inside the housing 60. The groove 42 in the link portion 40 in this case is positioned in the area of the support element 62, however, and is preferably also designed to be wider than in the first embodiment of the connector 10 so as to facilitate introducing a spring element.

Moreover, in the support element 62 a pouch, receiving portion or receptacle 63 is provided into which a spring element 50 can be inserted laterally, e.g. from the bottom. The spring element 50 again can be in the shape of a disk spring having a central opening and a segment-shaped recess (see FIG. 3) so that inside the groove 42 the spring element 50 can be slipped onto the link portion 40 with the recess facing upwards, the two lateral parts of the spring element 50 being spread apart. For producing an axial spring tension, the disk-shaped spring element 50 must be introduced into the receptacle 63 so that its outer edges are adjacent to the right inner surfaces of the receptacle 63 but the outwardly bent area is adjacent to the left inner surface of the groove 42 in the link portion 40. For this, the spring element 50 must be slightly compressed and bent, resp., upon insertion. The spring element 50 is then supported on the receptacle 63 and the link portion 40 so that it attracts the connecting element 20 to the support element 62 by its spring force.

The receptacle 63 is arranged at the support element 62 so that the spring element 50 can be introduced from outside into the receptacle 63 without for example the housing wall 60 having to be dismounted. For this purpose, at the spring element 50 again a grip element 56 or eyelet is provided by which the spring element 50 can be gripped from outside.

Figure 5:
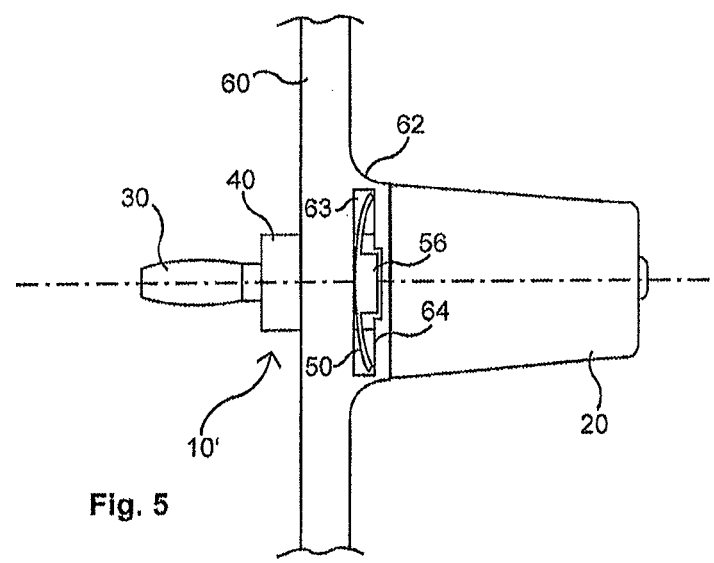
FIG. 5 a bottom view of a mounted connector according to FIG. 4.

The spring element 50 can be introduced laterally, e.g. from the bottom into the receptacle 63, wherein the receptacle 63 is substantially formed by a circumferential groove inside the support element 62 and an opening slit 64 in the lower area of the support element 62. This opening slit 64 is schematically visible from the bottom view of FIG. 5 and preferably permits inserting the spring element 50 together with the grip element 56, wherein the opening slit 64 should allow for a certain tolerance, for the spring element 50 might have to be somewhat twisted and bent so that it is adapted to be inserted into the receptacle 63 and the groove 42 in the link portion 40 according to instructions.

The opening slit 64 can also be arranged laterally or at the top of the support element 62 so that the spring element 50 accordingly can be slipped from a different direction onto the link portion 40. In any case, however, the support element 62 has to be considered part of the housing 60 so that also the arrangement of the spring element 50 within the support element 62 has to be considered an arrangement within the housing 60 for this invention.

Furthermore, means for covering the opening slit 64 can optionally be provided. For example, this can be an elastic rubber cover the geometry of which is adapted to the shape of the opening slit 64 so that it can be positively pressed into the opening slit 64 but is also easily removable again. However, it can also be provided, for example, that the outside of the support element 62 is provided with a male thread so that a lid having a central opening can be slipped over the Luer cone 20 and then can be screwed to the support element 62. The lid could also be fixed by individual detachable clipping and/or screwing connections at the housing 60 or it is merely an elastic ring or a rubber strap adapted to be slipped onto the periphery of the support element 62 so that it covers the opening slit 64.

The lid then would cover the opening slit 64 and could be removed again to dismount the spring element 50 and thus the connector 10'. A lid including screwed connection(s) to the supporting element might also be used to produce or reinforce the required spring tension in the spring element 50. In such embodiment the spring element 50 could be introduced more easily into a receptacle within the support element 62, because the required spring tension for an axial protection would not be generated before the lid is screwed on by the lid directly or indirectly exerting pressure on the spring element. In this case also the lid would have to be considered to be part of the housing, wherein wear and tear could occur at the screwed connection, however, so that the use of such lid has to be weighed against its drawbacks in a particular case. Moreover the opening slit 64 provided at the lower side of the link portion 40 could also be sufficiently protected against penetration of liquids/dirt and unauthorized access even without any additional cover.

The invention claimed is:

1. A connector for use in an opening of a housing of a medical device, the opening in the housing including a groove having a locking geometry, the connector comprising:
   a connecting element configured to receive and connect to a tube-shaped article outside the housing;
   a coupling including a hollow link portion adapted to be inserted through the opening of the housing to connect to the connecting element located outside of the housing, such that the hollow link portion of the coupling is partially located within the interior of the housing and protrudes from the opening of the housing to meet the connecting element, and the connecting element contacts the outer wall of the housing when the coupling and connecting element are interconnected, wherein:
   the hollow link portion of the coupling comprises means for rotary fixing of the connector inside the opening of the housing,
   the means for rotary fixing of the connector is a lug provided at the link portion having a complementary shape to the locking geometry of the groove, the lug is configured to interact with the groove via a tongue-and-groove connection to perform the rotary fixing when the hollow link portion of the coupling is fully inserted into the opening of the housing; and a spring element configured to produce a spring force in an axial direction and further configured to be detachably arranged at the link portion such that the connector is supported at the housing to be axially resilient via the spring element, and wherein:

the spring element is adapted to be radially slipped onto the link portion, wherein at the link portion at least one groove is provided for axially and positively fixing the spring element, the spring force produced by the spring element biases the connecting element against the outer wall of the housing, and the spring element is in the form of a disk spring or a leaf spring, includes a central opening and a segment-shaped slit reaching to the central opening, and is adapted to be spread for being put into the at least one groove.

2. The connector according to claim 1, wherein the connector is encoded in color by adding color particles.

3. A medical device for extracorporeal blood treatment comprising a housing, wherein the housing has at least one opening into which a coupling according to claim 1 is introduced.

4. The medical device according to claim 3, wherein the spring element is accessible from the outside of the housing.

5. The connector according to claim 1, wherein the connecting element is in the form of a male Luer cone.

* * * * *